(12) United States Patent
Levin

(10) Patent No.: US 6,677,321 B1
(45) Date of Patent: Jan. 13, 2004

(54) METHODS AND COMPOSITIONS FOR TREATMENT OF INFLAMMATORY DISEASE

(75) Inventor: Bruce Levin, One Independence Place, Philadelphia, PA (US) 19106

(73) Assignee: Bruce Levin, Philadelphia, PA (US)

( * ) Notice: Subject to any disclaimer, the term of this patent is extended or adjusted under 35 U.S.C. 154(b) by 0 days.

(21) Appl. No.: 09/724,645

(22) Filed: Nov. 28, 2000

Related U.S. Application Data

(60) Provisional application No. 60/169,845, filed on Dec. 9, 1999.

(51) Int. Cl.$^7$ .................. A61K 31/65; A61K 31/22; A01N 37/02; A01N 37/06
(52) U.S. Cl. .................. 514/154; 514/546; 514/549; 514/552; 554/223
(58) Field of Search .................. 514/506, 546, 514/152, 552, 154, 549; 554/223

(56) References Cited

U.S. PATENT DOCUMENTS

| | | | | |
|---|---|---|---|---|
| 4,049,824 | A | 9/1977 | Diehl | 424/312 |
| 4,113,881 | A | 9/1978 | Diehl | 424/312 |
| 5,260,066 | A | 11/1993 | Wood et al. | 424/447 |
| 5,308,839 | A | 5/1994 | Golub et al. | 514/152 |
| 5,569,676 | A | 10/1996 | Diehl | 514/549 |
| 5,874,479 | A | 2/1999 | Martin | 514/724 |
| 6,391,864 | B1 * | 5/2002 | Stone | 514/62 |
| 6,417,227 | B1 * | 7/2002 | Lord et al. | 514/529 |

FOREIGN PATENT DOCUMENTS

| | | |
|---|---|---|
| WO | WO 99/52508 | 10/1999 |
| WO | WO 00/64436 | 11/2000 |

OTHER PUBLICATIONS

Krause and Mahan. Food, Nutrition, and Diet Therapy: A Textbook of Nutritional Care 7$^{th}$ ed., pp. 40–51 and 850–876. W.B. Saunders Company (1984).*
Beluzzi et al., "Effects of New Fish Oil Derivative on Fatty Acid Phospholipid–Membrane Pattern in a Group of Crohn's Disease Patients" Digestive Diseases and Sciences, vol. 39(12), pp. 2589–2594 (Dec. 1994).*
Product Alert: "Integris Everlasting" mfgd. by Health Solutions. (Dec. 22, 1997).*
Cochran and Dent, "Cetyl Myristoleate—A Unique Natural Compound Valuable in Arthritis Conditions" pp. 70–74. Townsend Letter for Doctors and Patients. (Jul. 1997).*
Cochran, "Dr. Chuck Cochran Discusses Arthritis and Cetyl Myristoleate" entire publication. (©1996).*
Siemandi. "The effect of cis–9–cetyl myristoleate (cmo) and ajunctive therapy on the course of arthritic episodes in patients with various auto–immune diseases characterized by the common terminology, "arthritis"... " Manuscript, pp. 1–6 (1997).*
Goodman & Gilman's The Pharmacological Basis of Therapeutics 10ed. McGraw–Hill, pp. 1047 and 1048 (2002).*
Webster's II New Riverside University Dictionary. Houghton Mifflin Co, p. 127 (1994).*
The Merck Index, 11$^{th}$ ed. Merck & Co. Rahway, NJ, USA, pp. 26, 870, 4353 (1989).*
Wilson and Gisvold's Textbook of Organic Medicinal and Pharmaceutical Chemistry, 9$^{th}$ ed. J.B. Lippincott Co. pp. 723–732 (1991).*
"Tetracyclines Suppress Matrix Metalloproteinase Activity in Adjuvant Arthritis and in Combination with Fluribiprofen, Ameliorate Bone Damage" Greenwald et al, J. Rheumatology vol. 19(6), pp. 927–938 (1992).*
"Preliminary Study of the Safety and Efficacy of SC–58635, a Novel Cyclooxygenase 2 Inhibitor" Simon et al, Arthritis and Rheumatism, vol. 41(9), pp. 1591–1602 (1998).*
"Intraarticular Sodium Hyaluronate (Hyalgan) in the Treatment of Patients with Osteoarthritis of the Knee: A Randomized Clinical Trial" Altman et al, J. Rheumatology, vol.25(11), pp. 2203–2212 (1998).*

* cited by examiner

*Primary Examiner*—Mukund J. Shah
*Assistant Examiner*—Zachary C. Tucker
(74) *Attorney, Agent, or Firm*—Kenyon & Kenyon

(57) ABSTRACT

Compositions useful for treating inflammatory diseases including arthritis are disclosed which comprise cetyl myristoleate compounds or related compounds and at least one compound useful for treatment of inflammatory disease, such as tetracycline compounds, Cox-2 inhibitors, non-steroidal anti-inflammatory drugs (NSAIDs), corticosteroids, local anaesthetics, chelating agents, matrix metalloprotease inhibitors, inhibitors of inflammatory cytokines, glucosamine, chondroitin sulfate and collagen hydrolysate. Also disclosed are pharmaceutical compositions and methods of treatment for inflammatory disease and local inflammation and dermal irritation. Also disclosed are compositions including tetracycline and at least one compound useful for treatment of inflammatory disease.

25 Claims, No Drawings

METHODS AND COMPOSITIONS FOR TREATMENT OF INFLAMMATORY DISEASE

This application claims benefit of Ser. No. 60/169,845 filed Dec. 9, 1999.

The present invention provides compositions and methods for prevention and treatment of arthritis and other inflammatory and autoimmune diseases.

BACKGROUND OF THE INVENTION

The present invention relates to a method for treating inflammatory disease to prevent or delay the progression of the disease process or to alleviate the symptoms thereof. Diseases and disorders which have significant inflammatory components are ubiquitous. Skin disorders, bowel disorders, certain degenerative neurological disorders, arthritis, autoimmune diseases and other illnesses afflict many patients. In certain disorders, infectious agents may be directly or indirectly responsible for the entire disease process. In other disorders, an infectious or other agent may in some way facilitate an autoimmune or inflammatory response. For many patients, dietary or environmental factors may trigger an autoimmune or inflammatory response. In many patients genetic factors can play a key role. In the majority of cases, the causative elements have not been defined and many of the key pathophysiological components have not been elucidated. Accordingly, treatment options for the majority of these diseases is suboptimal.

Currently, steroids, nonsteroidal anti-inflammatory agents (NSAIDs), aspirin compounds and cancer chemotherapeutic immunosuppressive agents are often used. These agents often do not provide adequate symptomatic relief and are not believed to alter the natural progression of the disease. Indeed, some of these agents may make the disease worse. Furthermore, powerful side effects are found with most all of these therapies. Hence, there is a great need for safe and effective therapy for these disorders.

Cetyl myristoleate has been used for treatment of rheumatoid arthritis (Diehl, U.S. Pat. No. 4,113,881) and osteoarthritis (Diehl, U.S. Pat. No. 5,569,676), but there are many patients who do not achieve satisfactory results with this compound.

Tetracycline compounds have been found to weakly decrease collagenase and other enzyme activity and decrease certain kinds of cartilage damage found in canine models. However, human trials have been disappointing thus far. Side effects include dizziness gastrointestinal upset, nausea, and diarrhea.

SUMMARY OF THE INVENTION

The invention disclosed herein relates to the use of cetyl myristoleate (CMO) and CMO compounds in combination with other compounds useful for treating inflammatory disease. The invention is useful for protection against the development of arthritis and other inflammatory diseases and to provide relief of symptoms in individuals where such disease has been diagnosed. Cetyl myristoleate compounds have herein been found to be particularly useful when used in combination with components of accepted therapies. When used in this manner, cetyl myristoleate compounds can provide significant symptomatic relief.

Certain pharmaceutically active compounds or combinations thereof can be coadministered with CMO compounds, but can have significant adverse side effects. Coadministration with CMO compounds allows the use of reduced amounts of such treatment components and reduction or elimination of their undesired or detrimental side effects.

Certain therapies which provide relief from symptoms of inflammatory disease may not be effective for treating underlying causes of the disease. CMO compounds can be used to supplement those therapies to slow disease progression or to improve patient outcome.

The present invention further contemplates a composition comprising CMO compounds and a pharmaceutically acceptable vehicle as well as methods of treatment which comprise the use of those compositions.

The invention also relates to the use of tetracycline compounds in combination with other compounds useful for treating inflammatory diseases.

The invention discloses compositions and methods for topical treatment of inflammation resulting from envenomation or contact with other irritants. Such compositions comprise local anaesthetics, either alone, or in combination with one or more of proteases, steroids, tetracycline compounds, and CMO compounds. Such compositions may further comprise ingredients which enhance absorption.

DETAILED DESCRIPTION OF THE INVENTION

Compositions of the invention comprise CMO and/or CMO compounds in combination with another substance known or thought to be useful for treatment of inflammatory disease. As used herein, CMO compounds refers to cetyl myristoleate and related compounds. These related compounds are esters of an unsaturated fatty acid and an alcohol. Unsaturated fatty acids include, for example, palmitoleic acid, oleic acid, linoleic acid, arachidonic acid, nervonic acid and the like. Preferred unsaturated fatty acids have cis double bonds. Furthermore, preferred unsaturated fatty acids have 12 or more carbon atoms. The preferred alcohol is long chain. Long chain alcohols have 10 or more carbon atoms and can be linear or branched. As used herein the term "modified cetyl myristoleate compounds" refers to the CMO compounds of the invention other than cetyl myristoleate itself, as described above.

According to one embodiment, compositions of the invention are pharmaceutical compositions which include one or more CMO compounds and at least one additional compound having potential utility for treatment of arthritis and other related inflammatory, autoimmune diseases or inflammatory diseases. Examples include, for example, tetracycline compounds, doxycycline, NSAIDs, and Cox-2 inhibitors, steroids (e.g. cortisone), cancer chemotherapeutic agents, chelating agents such as EDTA, inhibitors of tumor necrosis factor (TNF)(e.g. Embrel®), metalloprotease inhibitors, glucosamine, chondroitin sulfate, methyl sulfonal methane (MSM), S-adenosylmethionine (SAME) or other sulfur or methyl group donors, and synovial fluid supplements (e.g. Synvisc® and Hyalagan®).

Accordingly, one composition of the present invention includes a CMO compound and at least one compound selected from the group consisting of a tetracycline compound, a Cox-2 inhibitor, a non-steroidal anti-inflammatory drug (NSAID), a corticosteroid, a chelating agent, a matrix metalloprotease inhibitor, an inhibitor of inflammatory cytokines (e.g., interleukin inhibitor, inhibitor of interleukin synthetases), a local anaesthetic, glucosamine, chondroitin sulfate and collagen hydrolysate. As used herein, tetracycline compounds include, but are not limited to, tetracycline, doxycycline, minocycline, tetracycline homologs and modified tetracycline compounds.

A second composition of the invention includes a tetracycline compound and at least one compound selected from the group consisting of a Cox-2 inhibitor, a corticosteroid, a chelating agent, a matrix metalloprotease inhibitor, an inhibitor of inflammatory cytokines (e.g., interleukin inhibitor, inhibitor of interleukin synthetases), a local anaesthetic, glucosamine, chondroitin sulfate and collagen hydrolysates.

According to another embodiment of the invention are compositions for the treatment of inflammatory diseases, which includes a modified cetyl or sphingo myristoleate compound, with or without an additional compound.

Compositions of the invention can be used for treatment of arthritis. The present invention is also applicable to other autoinflammatory diseases as well as degenerative bone and joint diseases including osteoarthritis, crystal arthritis and capsulitis and other arthropathies. Further, the methods and compositions can be used for treating tendonitis, ligamentitis and traumatic joint injury.

The invention further contemplates treatment of other inflammatory immune disorders, including but not limited to rheumatic diseases, allergic disorders, asthma, allergic rhinitis, skin disorders, gastrointestinal disorders such as Crohn's disease and ulcerative colitis, transplant rejection, poststreptococcal and autiommune renal failure, septic shock, systemic inflammatory response syndrome (SIRS), adult respiratory distress syndrome (ARDS) and envenomation.

The invention further contemplates utilizing CMO compounds alone or in combination with another compound for the treatment of inflammatory bowel disease. Poor gastrointestinal absorption following ingestion of a CMO compound leads to increased distal intraluminal delivery of these compounds to the distal gastrointestinal tract. Such action places the compound in direct topical proximity to diseased intestinal, colonic or rectal mucosa or other tissues.

In an embodiment of the present invention, the amount of a CMO compound to be administered per day is from about 25 mg to about 1000 mg. More preferably, the amount of the CMO compound is from about 75 mg to about 750 mg.

Tetracycline compounds affect protein synthesis and appear to have anti-inflammatory properties in addition to their anti-microbial properties which are useful for treatment of arthritis. For example, there are other antibiotics that may be useful, and perhaps even more effective at killing acne bacteria but tetracycline compounds are more effective in treating acne. It is believed by the inventor that this is a result of tetracycline's anti-inflammatory activity. The anti-inflammatory activity of tetracycline compounds make them useful for treating other inflammatory disorders, even in the absence of an infectious agent. Tetracycline compounds can inhibit enzymes associated with inflammatory diseases such as matrix metalloproteases (MMPs), collagenase, gelatinase and elastase. While it is widely thought that tetracycline compounds decrease enzyme activity by chelation, they may also decrease inflammation by decreasing production of proinflammatory or other compounds. Tetracycline compounds may be effective when used with other compounds in the treatment of inflammatory conditions.

As used herein, tetracycline compounds include tetracycline and modified tetracyclines which may or may not have altered biological activity. For example, modification at specific positions can lead to the loss of antimicrobial bioactivity. See, e.g. Mitscher, The Chemistry of Tetracyclines, p.211 (1978). Examples of modified tetracycline compounds are those which lack the dimethylamino group at position 4 and tetracycline compounds modified at the 2-carbon position to produce a nitrile. According to the invention, a variety of tetracycline compounds can be employed, including those having reduced antimicrobial activities provided they retain anti-inflammatory activity. Examples of preferred tetracycline compounds include, but are not limited to doxycycline, minocycline, 4-dedimethylaminotetracycline, 6-fluoro-6-demethyltetracycline and other chemically modified tetracycline compounds.

In a preferred embodiment, a composition of the invention comprises at least one CMO compound and at least one tetracycline compound. The amount of tetracycline compound used according to the invention is an amount effect for treating an inflammatory disease and need not be a dose used for antimicrobial treatments. When the tetracycline compound is doxycycline, the dose for a human can be from about 5–10 mg to about 800 mg daily. Similarly, other tetracycline compounds can be used in normally prescribed amounts or in lesser doses which maintain effectiveness but reduce unwanted side effects. For example, the amount of tetracycline compounds used can be from about 10 mg to about 1200 mg.

When using CMO compounds and tetracycline compounds in combination, the particular dosage combination to be used for any individual is easily determinable. For example, when determining effective dosage for the relief of pain of arthritis, the practitioner will start with a recommended dose of the tetracycline compound and then adjust the amounts of the components to determine the smallest dosage which provides effective pain relief. For example, in a preferred embodiment, where the tetracycline compound is doxycycline, doxycycline can first be administered in a daily dose of up to about 800 mg, followed by a reduction to a minimal effective amount. The minimal effective dose can be about 5–10 mg or lower. A preferred dose is about 100 mg. When the combination is administered, for example, to suppress development of an inflammatory disease, the minimal effective amount to be administered can be determined by monitoring symptoms of the disease and determining the smallest dose which results in symptom suppression. Symptoms of the disease can be monitored by any invasive or noninvasive means which is convenient for measuring relevant aspects of the disease. For example, where the disease is osteoarthritis or another inflammatory joint disease, progression can be measured by determining amounts of collagenase in synovial fluid, by X-rays, or by other well known evaluation procedures which are applicable to the disease. Higher doses may be needed to inhibit the actual progression of the disease process pathophysiology.

In another embodiment, the composition comprises at least one CMO compound and a NSAID or Cox-2 inhibitor. The amount of CMO compound to be administered per day is from about 25 mg to about 2000 mg. More preferably, the amount of CMO compound is from about 75 mg to about 750 mg. The amount of the NSAID or Cox-2 inhibitor to be administered for treatment of an inflammatory disease is an amount effective in combination with CMO compound to provide relief from pain or other symptoms of the disease, or to provide a significant reduction in one or more indications of disease progression. The NSAID may be selected from the various classes of such compounds, and include for example, salicylates such as acetylsalicylic acid, and diflunisal, acetic acids such as indomethacin, sulindac, tolmetin, diclofenac, and etodolac, propionic acids such as flurbiprofen, naproxen, ketoralac, and ketoprofen, fenamates such as meclofenamate, oxicams such as piroxicam, and oxindoles such as tenidap. Other NSAIDs and Cox-2 inhibitors contemplated by the invention include, but are not limited to ibuprofen, flosulide, diclofenac, meloxicam, Celecoxib (i.e. Celebrex® or SC-58635), and Rofecoxib (i.e. Vioxx®, 4-(4'-methylsulfonylphenyl)-3-phenyl-2-(5H) furan-2-one, or MK-0966).

In a further exemplary embodiment, the composition comprises at least one CMO compound, a tetracycline compound and a Cox-2 inhibitor. The amount of CMO compound to be administered per day is from about 25 mg to about 1000 mg. More preferably, the amount of CMO compound is from about 75 mg to about 750 mg. Where doxycycline is used as the tetracycline compound, the amount to be administered can be from about 5–10 mg to about 800 mg daily. The Cox-2 inhibitor is in an amount which, when combined with CMO compound and tetracycline compound, results in a relief of symptoms or a significant reduction in one or more indications of disease progression.

According to the invention, CMO compounds can be used in combination with corticosteroids for treatment of inflammatory diseases. Corticosteroids are commonly used for treatment of certain inflammatory diseases and conditions. For example, periarticular injection of methylprednisolone (Depo-Medrol) can be effective for treatment of clinical sacroiliitis in patients with seronegative spondylarthropathy. Glucocorticoids are potent anti-inflammatory agents that play an important role in the therapy of many patients with connective tissue diseases, including systemic lupus erythematosus, polymyalgia rheumatica, various types of vasculitis, and complications of rheumatoid arthritis. Glucocorticoids reduce the function of lymphocytes, monocytes, and eosinophils in peripheral blood and inhibit release of lysosomal enzymes. Glucocorticoids have proved to be effective in the treatment of inflammatory manifestations of disease, but long term dosing of increasing amounts are often required with their attendant side effects becoming common and severe.

Among significant adverse effects of glucocorticoid therapy which can be minimized by the use addition of CMO compounds or tetracycline compounds and the reduction in the amount of glucocorticoids are osteoporosis, aseptic necrosis of bone, steroid myopathy, diabetes and defective collagen synthesis.

Other potentially useful compounds for inflammatory disease treatment which can benefit from the inclusion of CMO compounds or tetracycline compounds in the treatment regimen include chelating agents such as EDTA, metalloprotease inhibitors and various inhibitors of synthesis or activity of immunostimulatory factors such as tumor necrosis factor (TNF) and IL-1. Activated oxygen species and other mediating substances from triggered phagocytes appear to exacerbate and perpetuate the rheumatoid condition. Iron excesses are capable of aggravating arthritic inflammation, probably through their pro-oxidant potentials. Iron chelating drugs and anti-oxidants have potential for clinical use to reduce free radical-induced tissue damage in rheumatoid arthritis.

Matrix metalloproteases (MMPs) are a family of enzymes that can degrade all the components of the extracellular matrix. To prevent unlimited connective tissue destruction a number of inhibitors exist to limit their activity. Artificial inhibitors which are useful for preventing cartilage erosion include cartilage protective agent (CPA) Ro 32-3555 (Roche) and CGS 27023A (Ciba Geigy).

Treatment with a chimeric mAb to TNF-alpha has been shown to suppress inflammation and improve patient well-being in rheumatoid arthritis (RA). Examples of TNF antagonists shown to be effective for short term treatment include infliximab and etanercept. In addition, antagonism of the cytokine IL-1 may be useful for prevention of joint destruction.

Combination therapy using effective doses of CMO compounds or tetracycline compounds with chelating agents, MMP inhibitors or inhibitors of inflammatory compounds is contemplated.

CMO compounds or tetracycline compounds can be used in combination with one or more nutraceutical agents. Many nutraceuticals are believed to possess biological activities which are useful for disease treatment. Several studies claim glucosamine, chondroitin sulfate and collagen hydrolysate to be somewhat useful for symptomatic treatment of osteoarthritis. In an embodiment of the invention, treatment with CMO compounds and tetracycline compounds will slow cartilage and tissue deterioration and increase the effectiveness of these and other nutraceutical agents or factors which stimulate new cartilage formation, presumably by decreasing cartilage destruction.

Typically, the amount of glucosamine or chondroitin sulfate administered per day ranges from about 500 mg to about 2500 mg. CMO compounds can be administered in combination with the aforementioned agents to obtain increased benefit, for example, where stronger remedial effects are desired. The amount of CMO compound to be administered per day is from about 25 mg to about 1000 mg. More preferably, the amount of CMO compound is from about 75 mg to about 750 mg. Tetracycline compounds can be added for increased effectiveness.

Viscosupplementation of synovial fluid has been used for treatment of arthritis patients. For example, treatment of synovial fluid of RA patients with intra-articularly injected hyaluronate has been found to result in clinical improvement. In addition, synthetic crosslinked hyaluronans having improved viscosity characteristics, such as hylan G-F 20 (Synvisc), have been developed as therapeutic agents. Viscosupplementation has also been tested in combination with treatment with NSAIDs. According to the invention, CMO compounds or tetracycline compounds are used in combination with such treatments in a dose from about 25 mg to about 1000 mg. More preferably, the amount of CMO compounds is from about 75 mg to about 750 mg.

With regard to arthritis and inflammatory joint diseases, treatment is indicated when joint disease is suspected from, for example, clinical or radiographic findings. Clinical signs of joint disease include lameness, pain, joint capsule distension, periarticular soft tissue swelling, crepitus, laxity, and thickening or enlargement of a joint by fibrosis or osteophytosis. Radiographic indications for arthroscopy include increased joint fluid, joint capsule thickening, periarticular soft tissue swelling, osteophyte formation, sclerosis, joint space narrowing, cartilaginous or osseous deformities or defects, bone chips or fragments, and joint laxity or subluxation.

Conditions which can diagnosed arthroscopically include osteochondritis dissecans (OCD) of the shoulder, and elbow, meniscal injuries, partial and complete cruciate ligament ruptures, fragmentation of the medial coronoid process, degenerative joint disease, intra-articular fractures, synovitis, bicipital tendonitis, bicipital tendon rupture, and neoplasia.

Cartilage lesions can be detected before the onset of degenerative joint disease. Obtaining biopsy specimens of synovial membrane from more than one joint with a minimally invasive technique is particularly helpful in the diagnosis of immune-mediated arthropathies.

It is discovered herein that certain local anaesthetics can be used to reduce symptoms of envenomation, particularly inflammation, when topically applied. In general, localized inflammation and dermal irritation can be similarly treated. Causes of such inflammation or irritation include, but are not limited to, contact with toxins, immunogens or other irritants. Although teatment of human subjects is exemplified, treatment of other mammals is contemplated as well.

Local anaesthetics include for example lidocaine, ropivicaine, prilocaine, americaine, benzocaine, bupivicaine, long acting topical anaesthetic (LTA; AstraZeneca), EMLA® (eutectic mixture of local anaesthetics; AstraZeneca) anaesthetics (from Astra Pharmaceuticals), and other eutectic mixtures of local anaesthetics. EMLAI® is a mixture of lidocaine and prilocaine in a ratio of about 1:1. It is understood that for compounds with a chiral center, levo, dextro or an optimum mixture may provide therapeutic benefit. For example, the levo form of ropivicaine and bupivicaine provide a degree of vasoconstriction relative to the dextro forms of these compounds.

In an embodiment of the invention, the local anaesthetic is used in combination with CMO compounds, tetracycline compounds, papain or other proteases or peptidases, steroids or topical antibiotics to reduce inflammation, pain or infection risk. The CMO compounds, tetracycline compounds, papain or other proteases or peptidases, steroids, or topical antibiotics can be topically applied or administered by another route. For such treatments, the local anaesthetic will usually be topically applied. Local anaesthetics typically are applied in amounts as are known in the pharmaceutical art and commonly used to deaden sensation. For topical application steroids are used in concentrations typically available in commercially available creams and salves and in an amount sufficient to cover the area to be treated. Tetracycline compounds are applied in amounts from about 10 $\mu$g to about 1000 $\mu$g. CMO compounds are useful when applied in amounts from about 25 $\mu$g to 500 $\mu$g. Proteases are typically formulated in ointments or other vehicles in an amount from 1% to 50% by weight.

It will be apparent that topical preparations may further comprise substances which enhance absorption. Such absorption enhancers are well known to those of ordinary skill in the art. Examples include, but are not limited to dimethyl sulfoxide (DMSO), fatty acids, micelles, and microsome and liposome preparations. Furthermore, DMSO or related compounds can have analgesic or anti-inflammatory properties.

Compositions can be administered by a variety methods which are well known in the art. Routes of administration include, but are not limited to oral, topical, sublingual, rectal, intranasal, intraocular, intravenous, intramuscular, transdermal, and by inhalation.

However, for delivery to specific sites of inflammation, other means can be used for administering the composition such as, for example, by intraarticular, periarticular or intraosseous injection. Delivery methods can employ microsomes or liposomes. Where desirable, active components can be formulated into timed-release products. Target specific delivery may be helpful as in colonic delivery of tetracycline compounds, CMO compounds, local anaesthetics or other agents to patients with colitis, or using transport peptides to bring effective compounds deeper into joint collagen or other tissues.

In addition, active components can be delivered locally to specific sites of action, for example by intraarticular, periarticular and intraosseous injection. For treatment of envenomation by insects or other animals, topical application of a proteolytic enzyme (e.g., papain or stromolysin, collagenase) and local anaesthetics is effective in relieving pain and decreasing inflammation. The addition of CMO compounds or tetracycline compounds to the therapy, applied topically or otherwise administered, can further increase efficacy.

There is no requirement that active components used in treatment be administered by the same route or at the same time. For example, in one embodiment, a tetracycline compound is administered orally according to a first schedule and CMO compound is administered orally according to a second schedule. In another embodiment, a tetracycline compound and a Cox-2 inhibitor are injected and a CMO compound is administered orally. In a further embodiment, viscosupplementation by intraarticular injection is combined with intraarticular administration of a CMO compound.

For the purposes of the invention, "pharmaceutically acceptable vehicle" means any of the standard pharmaceutical vehicles. Vehicles include any and all solvents, dispersion media, coatings, bandages, patches, antibacterial and antifungal agents, isotonic and absorption delaying or enhancing agents, transport polypeptides and lipids, sweeteners and the like. The pharmaceutically acceptable vehicles may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents with pharmaceutically active substances is well known in the art. Except insofar as any conventional media or agent is incompatible with the active ingredient, its use in the therapeutic compositions is contemplated. Supplementary active ingredients can also be incorporated into the compositions.

Examples of suitable vehicles are well known in the art and include, but are not limited to, any of the standard vehicles such as phosphate buffered saline, phosphate buffered saline containing Polysorb, water, emulsions such as oil/water emulsion, and various types of wetting agents. In a preferred embodiment, pharmaceutical compositions of the invention are for administration to a human. Alternatively, a pharmaceutical composition can be administered to any animal.

In the case of treatment of joint diseases, it is helpful to reduce forces exerted on affected tissues. For example, treatment of joint diseases according to the invention can include reduction of gravitational or other forces acting on the affected joint or at vulnerable locations of the affected joint. External tractions or mechanical support devices (e.g., specially shaped foam or other viscoelastic compositions) which decrease forces acting on the affected joint will be helpful. Splinting of the hand to maintain a joint in a neutral position can help treatment of joints of the hand. Similarly, other joints can be appropriately supported.

For reduction of inflammation and associated discomfort, increasing ambient pressure, for example, by using hyperbaric devices, submersion, or other means, can also be used to increase the effects of the treatments described herein.

Throughout this application, various publications, patents, and patent applications have been referred to. The teachings and disclosures of any publications, patents, and patent applications referred to hereins are hereby incorporated by reference, in their entireties, into this application to more fully describe the state of the art to which the present invention pertains.

It is to be understood and expected that variations in the principles of invention herein disclosed may be made by one skilled in the art and it is intended that such modifications are to be included within the scope of the present invention.

Examples of the invention which follow are set forth to further illustrate the invention and should not be construed to limit the invention in any way.

EXAMPLE 1

Treatment of Arthritis with a CMO Compound and a Tetracycline Compound

A middle-aged female who suffered from knee arthritis and did not respond well to CMO therapy. NSAID drugs gave some relief, but pain was still severe. NSAID therapy was halted and tetracycline therapy was added. Rapid and effective symptomatic control was obtained. When tetracycline or CMO treatment was discontinued, symptoms worsened despite increase in dose of the remaining agent. Maximum relief was obtained with a combination of a tetracycline compound and a CMO compound.

EXAMPLE 2

Treatment of Arthritis with a CMO Compound and Doxycycline

A femal senior citizen who suffered from ankle and knee arthritis pain obtained no or minimal relief with CMO therapy. Doxycycline was added with excellent results noted. Symptoms returned when CMO compound or doxycycline was discontinued.

EXAMPLE 3

Treatment of Arthritis with a CMO Compound and Doxycycline

Doxycycline therapy was used for treatment of a middle aged male suffering from bilateral hip arthritis and experiencing severe pain despite increasing doses of NSAIDs. Rapid relief of pain to a more acceptable level was obtained with the addition of doxycycline but gastrointestinal upset was problematic. Cox-2 inhibitors were substituted for the NSAID agents with better results. However, over time, it was necessary to increase the doses of both agents to two to three times the initial dose in order to maintain adequate symptomatic relief. Side effects noted at that time included dizziness, nausea and abdominal pain. A CMO compound was added and the dosage of the other agents decreased to initial levels. The side effects disappeared and improved symptomatic relief was noted. The Cox-2 agent was discontinued with no increase in severity of symptoms. Attempts to discontinue doxycycline were unsuccessful, with symptoms increasing during doxycycline free periods. Similarly, attempts to discontinue CMO treatment were met with worsening symptomatology.

EXAMPLE 4

Relief of Venom Induced Inflammation

Different bee stings on the same individual were treated by two different methods. A bee sting on one arm was treated with papain with mild relief from pain and swelling. A second bee sting on the other arm was treated with papain, a eutectic mixture of local anaesthetics (EMLA®) and a topical steroid (Kenalog). Relief from pain was excellent and swelling was significantly reduced. The improved relief from pain was apparent even after all other sensation had returned to normal in the area which received the EMLA® treatment.

What is claimed is:

1. A pharmaceutical composition for treating an inflammatory disease comprising an effective amount of at least one cetyl myristoleate compound and an effective amount of at least one compound useful for treating inflammatory disease selected from the group consisting of a tetracycline compound, a nonsteroidal anti-inflammatory drug, a Cox-2 inhibitor, a corticosteroid, S-adenylmethionine, and a synovial fluid supplement.

2. The composition of claim 1 wherein the at least one CMO compound comprises one or more esters of unsaturated fatty acids and alcohols.

3. The composition of claim 2 wherein the unsaturated fatty acid has 12 or more carbon atoms and cis double bonds and the alcohol has 10 or more carbon atoms.

4. The composition of claim 1 wherein the CMO compound is present in an amount from about 25 mg to about 1000 mg.

5. The composition of claim 1 wherein the CMO compound is present in an amount from about 75 mg to about 750 mg.

6. The composition of claim 1, wherein the at least one compound useful for treating inflammatory disease comprises a tetracycline compound and a Cox-2 inhibitor.

7. The composition of claim 1 wherein the CMO compound is cetyl myristoleate.

8. The composition of claim 1, wherein the compound useful for treating inflammatory disease is a tetracycline compound selected from the group consisting of tetracycline, doxycycline, minocycline, 4-dedimethylaminotetracycline, and 6-fluoro-6-demethyltetracycline.

9. The composition of claim 1, wherein the compound useful for treating inflammatory disease is a nonsteroidal anti-inflammatory drug or Cox-2 inhibitor selected from the group consisting of acetylsalicyclic acid, diflunisal, indomethacin, sulindac, tolmetin, diclofenac, etodolac, flurbiprofen, naproxen, ketoralac, ketoprofen, meclofenamate, piroxicam, tenidap, ibuprofen, flosulide, diclofenac, meloxicam, Celecoxib and Rofecoxib.

10. The composition of claim 1, wherein the compound useful for treating inflammatory disease is a corticosteroid.

11. The composition of claim 1, wherein the compound useful for treating inflammatory disease is S-adenosylmethionine.

12. The composition of claim 1, wherein the compound useful for treating inflammatory disease is a synovial fluid supplement selected from the group consisting of sodium hyaluronate and hylan GF 20.

13. A method of treating an inflammatory disease which comprises administering to a mammal a composition comprising at least one cetyl myristoleate (CMO) compound and at least one compound useful for treating inflammatory disease selected from the group consisting of a tetracycline compound, a nonsteroidal anti-inflammatory drug, a Cox-2 inhibitor, a corticosteroid, S-adenylmethionine, and a synovial fluid supplement, for a time and in an amount effective to treat the inflammatory disease.

14. The method of claim 13 wherein the CMO compound is cetyl myristoleate.

15. The method of claim 13, wherein the cetyl myristoleate compound is in a daily amount from about 25 mg to about 1000 mg.

16. The method of claim 13, wherein the cetyl myristoleate compound is in a daily amount from about 75 mg to about 750 mg.

17. The method of claim 13, wherein the compound useful for treating inflammatory disease is a tetracycline compound selected from the group consisting of tetracycline, doxycycline, minocycline, 4-dedimethylaminotetracycline, and 6-flouro-6-demethyltetracycline.

18. The method of claim 17, wherein the tetracycline compound is doxycycline in a daily amount from about 5 mg to about 800 mg.

19. The method of claim 17, wherein the cetyl myristoleate compound is in a daily amount from about 25 mg to about 1000 mg and doxycycline is in a daily amount from about 5 mg to about 800 mg.

20. The method of claim 13, wherein the at least one compound useful for treating inflammatory disease comprises a tetracycline compound and a Cox-2 inhibitor.

21. The method of claim 13, wherein the compound useful for treating inflammatory disease is a nonsteriodal anti-inflammatory drug or Cox-2 inhibitor selected from the group consisting of acetylsalicyclic acid, diflunisal, indomethacin, sulindac, tolmetin, diclofenac, flurbiprofen, naproxen, ketoralac, ketoprofen, meclofenamate, piroxicam, tenidap, ibuprofen, flosulide, diclofenac, meloxicam, Celecoxib and Rofecoxib.

22. The method of claim 13, wherein the compound useful for treating inflammatory disease is a corticosteriod.

23. The method of claim 13, wherein the compound useful for treating inflammatory disease is S-adenylmethonine.

24. The method of claim 13, wherein the compound useful for treating inflammatory disease is a synovial fluid supplement selected from the group consisting of sodium hyaluronate and hylan GF 20.

25. The method of claim 13, wherein the inflammatory disease is an inflammatory joint disease, the compound useful for treating an inflammatory disease is a synovial fluid supplement, and the composition is administered by intraarticular injection.

* * * * *